(12) United States Patent
Luo et al.

(10) Patent No.: US 10,463,463 B2
(45) Date of Patent: Nov. 5, 2019

(54) ELECTRIC TOOTHBRUSH HANDLE AND ELECTRIC TOOTHBRUSH

(71) Applicant: NINGBO SEAGO ELECTRIC CO., LTD, Ningbo (CN)

(72) Inventors: Ning Luo, Ningbo (CN); Yanzhong Cai, Leping (CN); Lingjun Guo, Gansu Province (CN)

(73) Assignee: NINGBO SEAGO ELECTRIC CO., LTD, Ningbo (CN)

( * ) Notice: Subject to any disclaimer, the term of this patent is extended or adjusted under 35 U.S.C. 154(b) by 388 days.

(21) Appl. No.: 15/374,188

(22) Filed: Dec. 9, 2016

(65) Prior Publication Data
US 2017/0360539 A1    Dec. 21, 2017

(30) Foreign Application Priority Data

Jun. 15, 2016    (CN) .......................... 2016 1 0435413

(51) Int. Cl.
*A61C 17/22*    (2006.01)
*A46B 15/00*    (2006.01)
*A61C 17/16*    (2006.01)

(52) U.S. Cl.
CPC ........ *A61C 17/225* (2013.01); *A46B 15/0044* (2013.01); *A61C 17/16* (2013.01); *A61C 17/221* (2013.01)

(58) Field of Classification Search
CPC ..... A61C 17/22; A61C 17/221; A61C 17/225; A46B 5/00; A46B 15/00; A46B 15/0002; A46B 15/0004; A46B 15/0038; A46B 15/0044; B25G 1/00

USPC ............................ 15/22.1, 105, 143.1, 167.1
See application file for complete search history.

(56) References Cited

U.S. PATENT DOCUMENTS

| | | | |
|---|---|---|---|
| 2011/0247158 A1* | 10/2011 | Jungnickel | G09F 13/06 15/167.1 |
| 2014/0007361 A1* | 1/2014 | Nazaroff | A46B 15/0044 15/22.1 |
| 2019/0008620 A1* | 1/2019 | Greer, Jr. | F21V 33/004 |

FOREIGN PATENT DOCUMENTS

JP    2011-200451    * 10/2011

* cited by examiner

*Primary Examiner* — Mark Spisich
(74) *Attorney, Agent, or Firm* — Schmeiser, Olsen & Watts LLP

(57) ABSTRACT

The invention relates to an electric toothbrush handle and an electric toothbrush. The electric toothbrush handle comprises: a shell, in the inner cavity of which at least one light emitting element is arranged; and a shading part, comprising a light transmission plate arranged on the periphery of the at least one light emitting element, and a first coating arranged on the outer surface and/or the inner surface of the light transmission plate; wherein a light transmission area in a set shape is formed at a position corresponding to each light emitting element in the first coating; and the light of the light emitting element is capable of penetrating through the light transmission area so that the shape of the light transmission area is visible via the shell. The electric toothbrush handle can avoid damage and even failure of a display mark due to wear thereof.

12 Claims, 6 Drawing Sheets

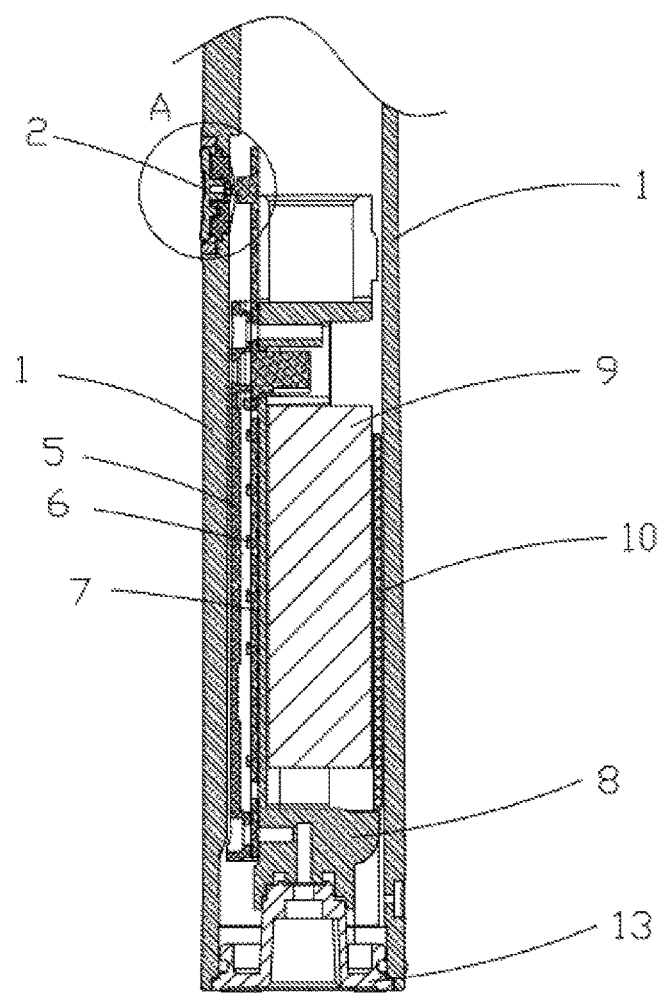
Fig. 3-a
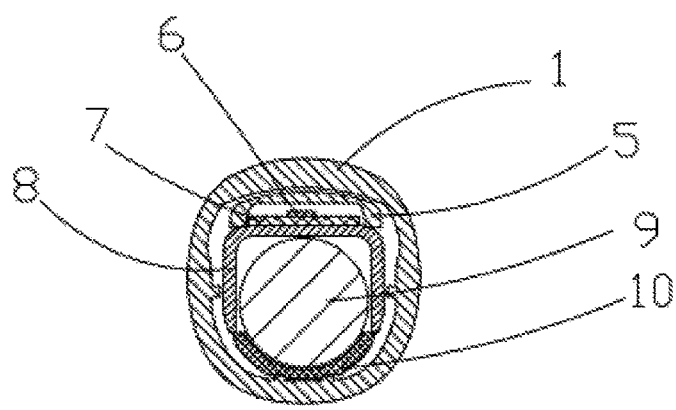
Fig. 3-b

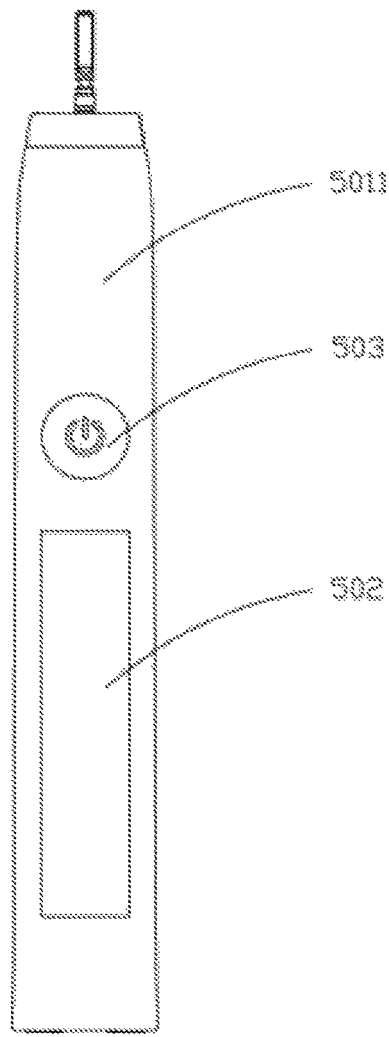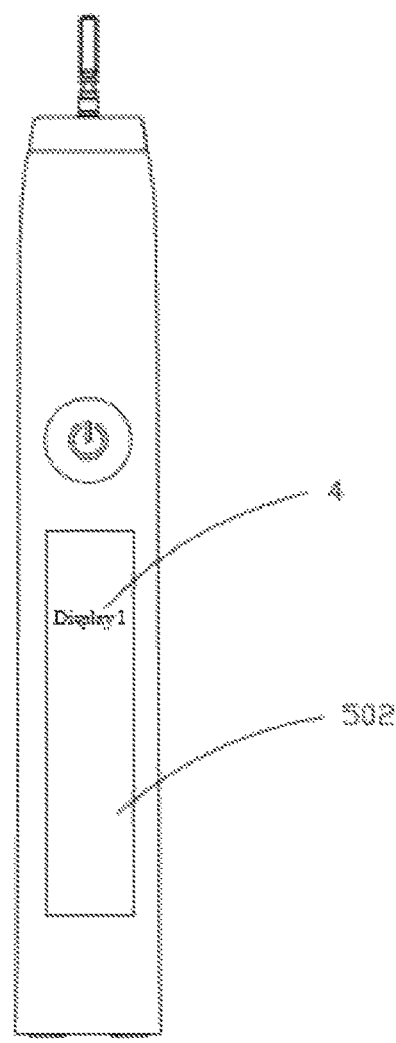
Fig. 5-a　　　　　　　　　　　　　　　　　Fig. 5-b

ELECTRIC TOOTHBRUSH HANDLE AND ELECTRIC TOOTHBRUSH

FIELD OF THE INVENTION

The present invention relates to the field of oral health, and particularly relates to an electric toothbrush handle and an electric toothbrush.

BACKGROUND OF THE INVENTION

An electric toothbrush serves as a personal care appliance in the field of oral health, and the brush head vibrates at a high frequency via quick rotation or vibration of an electric movement, decomposes toothpaste into superfine foams and then cleans teeth deeply. Compared with a common toothbrush, the electric toothbrush has the advantages of clearing dental plaque more thoroughly as well as reducing oral diseases including gingivitis, periodontal disease, gingival bleeding and the like more scientifically and effectively, and thus is gradually favored by consumers.

With respect to its structure, the electric toothbrush is mostly provided with a user interface on the surface, and the user interface is mainly used for displaying information indication associated with the operating mode of the toothbrush. For example, the operating mode can be current clean degree, and the associated information indication can be brush head speed (or speed change rule), cleaning time and the like under the clean degree.

In most of the current user interfaces, a coating is arranged on the handle, and then a mark for characterizing corresponding meanings is machined on the coating by way of laser or the like, so that the mark cannot be flexibly changed, and the mark is prone to damage, e.g., wear and the like, to different degrees after a certain time of use.

SUMMARY OF THE INVENTION

Technical Problem

In view of this, the technical problem to be solved by the present invention is how to avoid the damage of a display mark (e.g., characters, a pattern, etc.) while the display function of an electric toothbrush handle is realized.

Solution

In order to solve the above technical problem, according to one embodiment of the present invention, provided is an electric toothbrush handle, including:
a shell, in the inner cavity of which at least one light emitting element is arranged; and
a shading part, including:
a light transmission plate arranged on the periphery of the at least one light emitting element, and
a first coating arranged on the outer surface and/or the inner surface of the light transmission plate;
wherein a light transmission area in a set shape is formed at a position corresponding to each light emitting element in the first coating; and
the light of the light emitting element is capable of penetrating through the light transmission area so that the shape of the light transmission area is visible via the shell.

For the above electric toothbrush handle, in one possible implementation, the shell is of a transparent structure.

For the above electric toothbrush handle, in one possible implementation, the electric toothbrush handle further includes a second coating which is arranged on the outer surface and/or the inner surface of the shell, and the light of the light emitting element is capable of penetrating through the light transmission area and is visible via the second coating and the shell.

For the above electric toothbrush handle, in one possible implementation, a driving control part is also arranged in the shell, and includes:
a motor, with a power output end connected with a brush head installed on the electric toothbrush handle, and used for driving the brush head into motion; and
a control panel, used for controlling the motor and the light emitting element.

For the above electric toothbrush handle, in one possible implementation, the light transmission plate and the light emitting element are both fixed on the control panel.

For the above electric toothbrush handle, in one possible implementation, a support is also arranged in the shell; wherein one side of the support is provided with a batter holder which is matched with a battery cover to form an installation space for a battery;
the control panel is fixed on the other side of the support; and
the tail end of the support is axially limited via a bottom cover.

For the above electric toothbrush handle, in one possible implementation, at least one switch for selecting a target working mode is also arranged on the shell, and the switch is electrically connected with the control panel.

In order to solve the above technical problem, according to another embodiment of the present invention, provided is an electric toothbrush, including an electric toothbrush handle and at least one brush head which can be installed at one end of the electric toothbrush handle, and the electric toothbrush handle is the aforementioned one.

Beneficial Effects

According to the electric toothbrush handle in the embodiment of the present invention, the light of the light emitting element penetrates through the light transmission area on the second coating, so that the shape (mark) corresponding to the light transmission area is visible. The light transmission area in set shape is arranged on the second coating of the shading part, belongs to the internal structure of the handle, and thus avoids damage and even failure due to wear of the handle, and the (first or second) coating can be selectively arranged on a corresponding carrier according to practical situations, that is, the outer side or the inner side of the shading plate and the shell, so the design is flexible.

In the process of realizing the display function of the electric toothbrush with the electric toothbrush handle, the first coating arranged on the shell is merely used as a projection screen, so a hole is not needed in the display area of the shell, and thus the water ingress phenomenon of the electric toothbrush is effectively avoided.

Other features and aspects of the present invention will become apparent from the following detailed description of the exemplary embodiments with reference to the accompanying drawings.

BRIEF DESCRIPTION OF THE DRAWINGS

The accompanying drawings included in the specification and constituting a part of the specification, together with the specification, illustrate the exemplary embodiments, features and aspects of the present invention, and are used for interpreting the principle of the present invention.

FIG. 3-*a* shows a sectional schematic diagram I of the electric toothbrush handle in one embodiment of the present invention (in the axial direction);

FIG. 3-*b* shows a sectional schematic diagram II of the electric toothbrush handle in one embodiment of the present invention (in the radial direction);

FIG. 5-*a* shows an application schematic diagram I of an electric toothbrush in another embodiment of the present invention (the light emitting element is not lit up);

FIG. 5-*b* shows an application schematic diagram II of the electric toothbrush in another embodiment of the present invention (the light emitting element is lit up);

Figure 1:
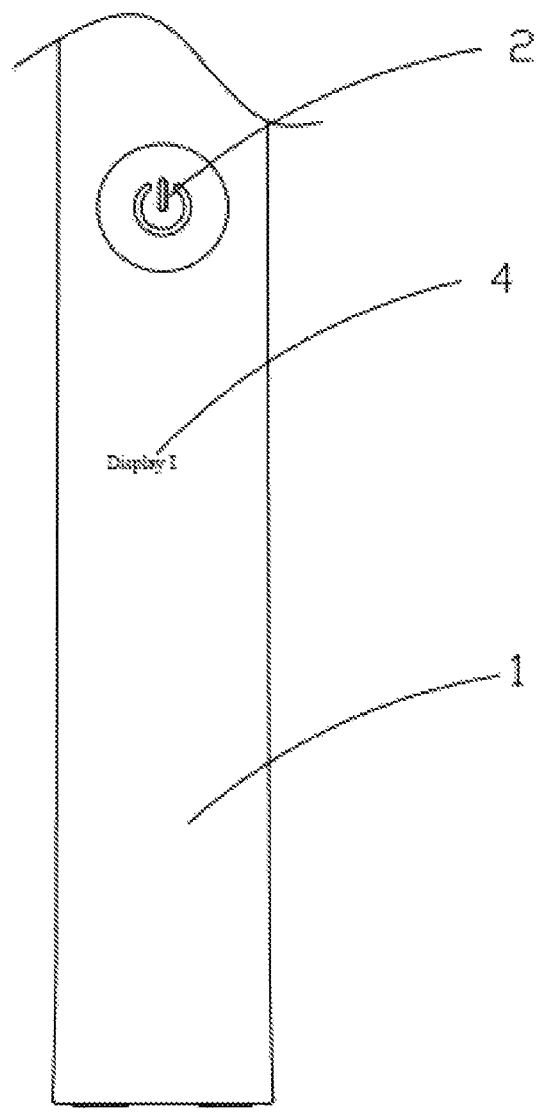
FIG. 1 shows a schematic structural diagram of an electric toothbrush handle in one embodiment of the present invention.

REFERENCE SIGNS 1, shell
2, button
21, button ring
22, soft rubber
3, light transmission area
4, mark
5, light transmission plate
6, light emitting element
7, control panel
8, support
9, battery
10, battery cover
11, first coating
12, second coating
13, bottom cover
501, handle area
502, display area
503, button area

DETAILED DESCRIPTION OF THE EMBODIMENTS

Various exemplary embodiments, features and aspects of the present invention will be described in detail below with reference to the accompanying drawings. The same signs in the drawings represent elements with the same or similar functions. Although various aspects of the embodiments are illustrated in the drawings, the drawings do not need to be drawn to scale unless otherwise indicated.

The special word "exemplary" herein means "using as an example or an embodiment or illustrative". Any "exemplary" embodiment described herein should not be interpreted as being superior to or better than other embodiments.

In addition, numerous specific details are given in the specific embodiments below in order to better illustrate the present invention. Those skilled in the art should understand that the present invention can also be implemented without some specific details. In some embodiments, the methods, means and circuits well known to those skilled in the art are not described in detail, thereby highlighting the theme of the present invention.

Embodiment 1

Figure 2:
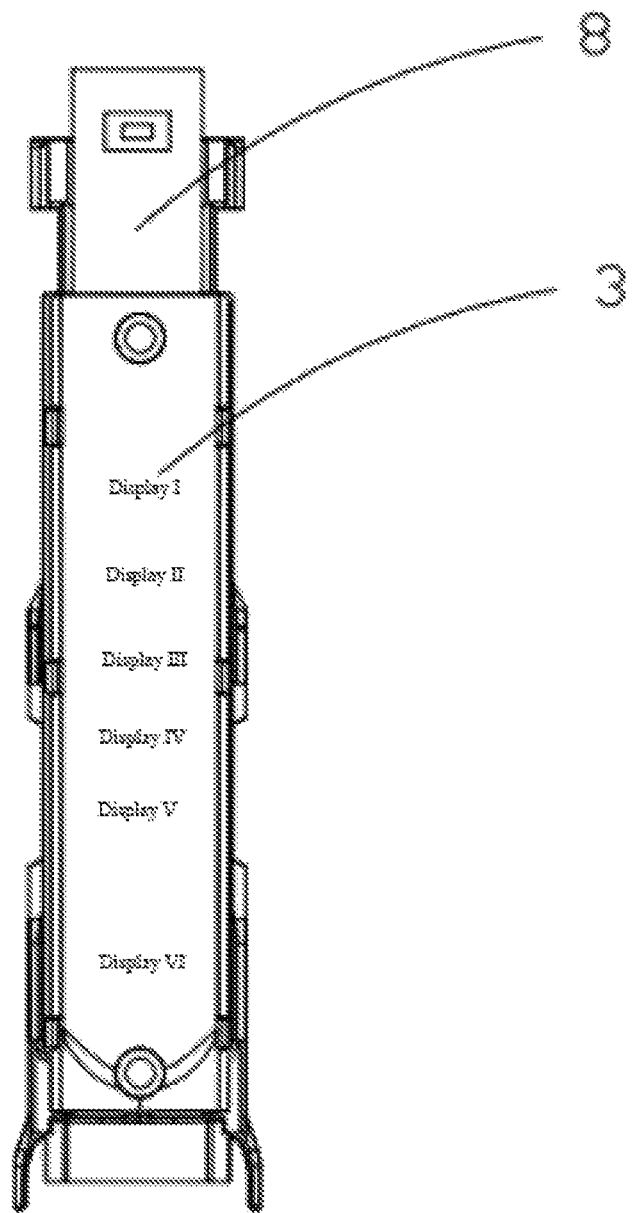
FIG. 2 shows a schematic structural diagram of internal components of the electric toothbrush handle in one embodiment of the present invention.
Figure 4:
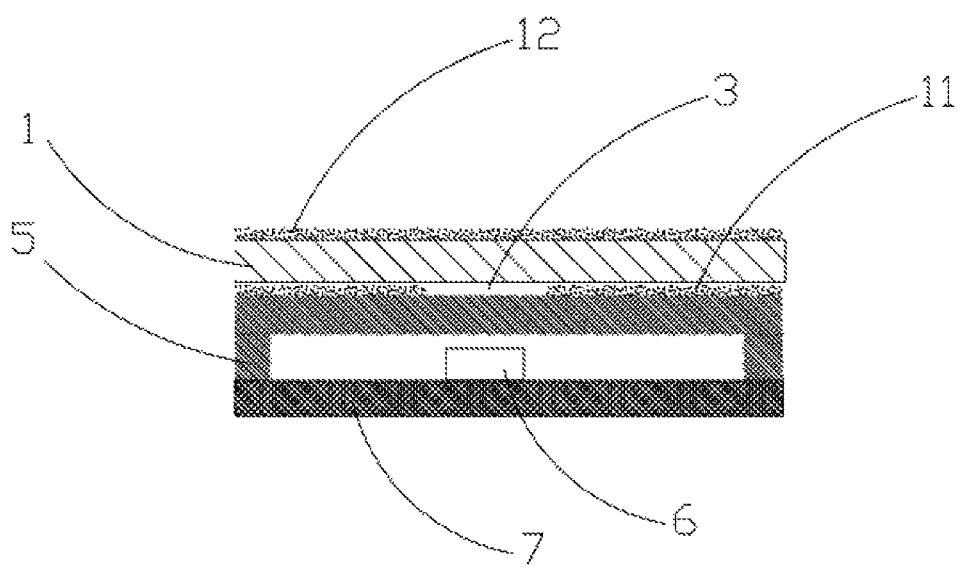
FIG. 4 shows a schematic diagram of coating arrangement of the electric toothbrush handle in one embodiment of the present invention.

FIG. 1 shows a schematic structural diagram of an electric toothbrush handle in one embodiment of the present invention. FIG. 2 shows a schematic structural diagram of internal components of the electric toothbrush handle in one embodiment of the present invention. FIG. 3-*a* and FIG. 3-*b* respectively show sectional schematic diagrams of the electric toothbrush handle in the axial direction and the radial direction. FIG. 4 shows a schematic diagram of coating arrangement for realizing the display function of the electric toothbrush handle.

As shown in FIG. 1 and FIG. 4, the electric toothbrush handle mainly includes:

a shell 1, in the inner cavity of which at least one light emitting element 6 is arranged; and a shading part, including:

a light transmission plate 5 arranged on the periphery of the light emitting element 6, and a first coating 11 arranged on the outer surface and/or the inner surface of the light transmission plate 5;

wherein a light transmission area 3 in a set shape (including but not limited to a character or a pattern) is formed at a position corresponding to each light emitting element 6 in the first coating 11; and the light of the light emitting element 6 can penetrate through the light transmission area 3 so that the shape of the light transmission area 3 is visible via the shell 1.

In a specific implementation, the first coating 11 is made of a light tight material and may be a nontransparent layer of black or other deep ink or the like, the area (roughly the right above area) corresponding to each light emitting element 6 is an area of a mark 4, the aforementioned light transmission area 3 in specific shape is machined (e.g., etched) at the corresponding position, the light of the light emitting element 6 penetrates through the light transmission area 3 to form a mark 4 corresponding to the shape of the light transmission area 3, and the first coating 11 except for the light transmission area 3 can shade the light of the light emitting element 6 and reliably limit the light penetrating through the light transmission area 3 within the range for forming the mark 4.

In a specific implementation, a part of or the whole of the shell 1 can be made of a light transmission material (e.g., a transparent structure). The outer surface and/or the inner surface of the shell 1 can be covered by a second coating 12. The second coating 12 has certain light transmission property, one the one hand can ensure that the mark 4 formed by the light of the light emitting element 6 on the coating can transmit information to a user, and one the other hand, can also shade ambient light, that is, ensure that the user cannot see the internal structure (e.g., a light transmission plate 5, a control panel, a motor and the like as mentioned below) of the shell 1 as much as possible, so as to improve the user experience. For example, the second coating 12 can be a coating with certain color, e.g., the second coating 12 is formed on the whole of the outer surface or the inner surface of the shell 1 (in a coating manner). As another example, only the corresponding position of the light transmission area 3 is coated with the second coating 12, and in this case, the user can see the internal structure of the shell 1. No matter how the arrangement position and the range of the second coating 12 are adjusted, it at least can ensure that the light of the light emitting element 6 can penetrate through the light transmission area 3 and is projected to the second coating 12 serving as a projection screen to form a mark 4 corresponding to the shape of the light transmission area 3, and ensures that the mark 4 can be displayed to the user via the second coating 12 based on the light transmission attribute of the second coating 12, so that the mark 4 is visible.

The light emitting element 6 may be an LED lamp or other component with a light emitting function.

With reference to FIGS. 2, 3-*a* and 3-*b*, the internal components arranged in the inner cavity of the shell 1 mainly include a driving control part, which is mainly used for driving a brush head connected with it into motion; the driving control part includes:

a motor, with a power output end extending out of the front end of the electric toothbrush handle and connected with the brush head, and used for driving the brush head to swing; and a control panel 7, used for controlling the motion parameters of the motor, and enabling the mark 4 projected to the second coating 12 to give indication information for characterizing a target working mode, that is, projecting the light transmission area 3 etched on the first coating 11 and corresponding to the target working mode to the second coating 12 serving as a projection screen by lightening the corresponding light emitting element 6 to form a mark 4, and further, the mark is made visible to a user via the light transmission performance of the second coating 12. (Taking an implementation having the coatings (11 and 12) as an example) specifically:

The electric toothbrush handle is provided with at least one switch (e.g., may be a button 2 for pressing operation), and the button 2 is electrically connected with the control panel 7 and is used for triggering the control panel 7 to emit an instruction of selecting one of a plurality of working modes as a target working mode, or an instruction of switching from the current working mode to the target working mode. According to the instruction, on the one hand, the motor responds to the instruction of the control panel 7 to drive the brush head to accomplish a series of motion (e.g., vibration) adapted to the target working mode according to set control parameters and/or a parameter group. On the other hand, the corresponding light emitting element 6 is lit up, and the light penetrates through the corresponding light transmission area 3 to project the transmitted information to the second coating 12 to form a mark 4 in a corresponding shape. As mentioned above, the second coating 12, due to certain light transmission property, can transmit indication information (e.g., a mode mark, motion parameters of the brush head, etc.) associated with the target working mode to a user. As a specific implementation, both the light emitting element 6 and the light transmission plate 5 are both fixed on one side, for displaying information, of the control panel 7 close to the handle, and specifically, the light transmission plate 5 roughly can be of a cover structure.

Moreover, the internal components arranged in the shell 1 further include:

a power supply, which can supply power to the light emitting element 6, so that the light emitting element 6 emits light to realize the display function of the handle. The power supply can also supply power to the driving control part, so as to drive the brush head into motion. The power supply can be realized in various ways, can be various types batteries or transformers or the like, and can be flexibly selected according to actual application requirements.

In one possible implementation, the power supply is a battery 9. In this case, one side of a support 8 also serving as an internal component is matched with a battery cover 10 to form an installation space for the battery 9.

The control panel 7 is fixed on the other side of the support 8 (the side for displaying information close to the handle).

Moreover, the tail end of the support 8 axially limits the internal components via a bottom cover 13 arranged at the rear end (the end opposite to the installed brush head) of the shell 1.

It should be noted that although the electric toothbrush is introduced above using an example that the first coating 11 is applied to the outer surface of the light transmission plate 5 and the second coating 12 is applied to the outer surface of the shell 1, as shown in the figures, those skilled in the art could understand that the present invention should not be limited thereto. In fact, a user completely can flexibly configure the specific way of arrangement of the coatings and the corresponding carriers according to personal preference and/or practical application scenarios, as long as the light transmission performance and the accuracy of the projection relation are guaranteed.

As mentioned above, the mark 4 in the present invention can be formed by the steps of arranging (e.g., spray coating or pasting) the first coating 11 on the outer side or the inner side of the light transmission plate 5, and then peeling off the first coating 11 according to a set shape in the area corresponding to the light emitting element 6 by laser engraving, wherein the shape of the peeled light transmission area 3 is consistent with the mark 4 formed on the second coating 12. Because the light transmission area 3 is formed inside the shell 1 and is not worn, the phenomena of damage and even failure of the mark 4 and the like due to wear of the handle are avoided.

Moreover, because the light transmission area 3 for forming the mark 4 is machined on the light transmission plate 5, the process is obviously simplified relative to the process of directly forming the mark 4 on the shell 1.

Embodiment 2

Figure 6:
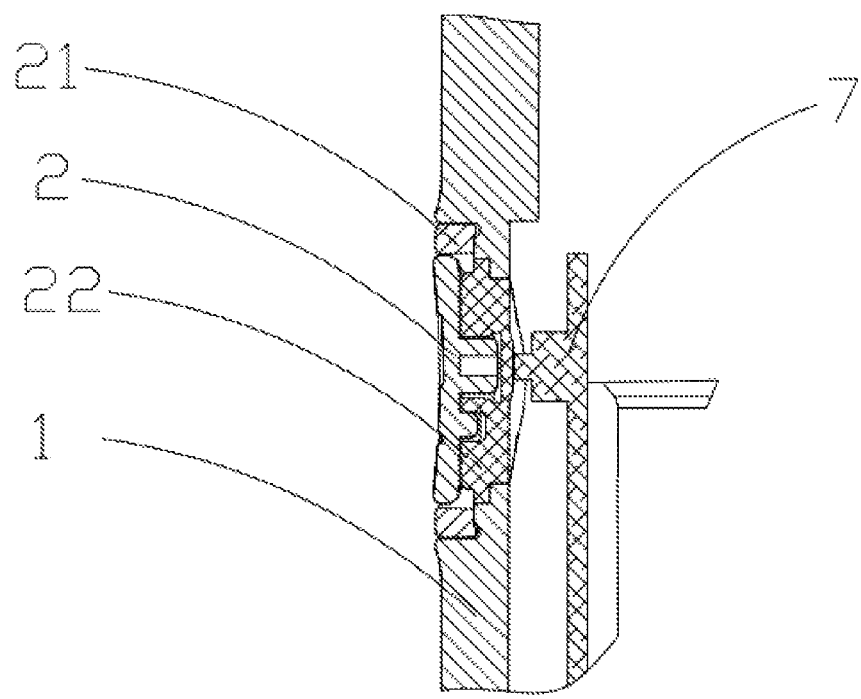
FIG. 6 shows a partial schematic diagram (A) of FIG. 3-*a*.

FIGS. 5-*a* and 5-*b* show another embodiment of the present invention, that is, a schematic diagram of an application structure of an electric toothbrush with the aforementioned electric toothbrush handle. Specifically, FIGS. 5-*a* and 5-*b* respectively show application schematic diagrams of the electric toothbrush when the light emitting element 6 is lit up and not lit up. In a specific application example, the electric toothbrush mainly includes a handle area 501, a display area 502 and a button area 503. FIG. 6 shows an improvement solution of the button area 503 of the electric toothbrush.

The electric toothbrush mainly includes the aforementioned electric toothbrush handle and at least one brush head which can be installed at one end of the electric toothbrush handle, e.g., may having a multi-brush-head replaceable structure. The brush head is mainly used for cleaning the teeth of a user. The brush head can also be used for cleaning other oral parts such as tongue and the like according to personal use habit and the specific design of the brush head, or cleaning other reasonable parts in non-oral environments, of course.

Thus, when the light emitting element 6 is not lit up or the electric toothbrush is in a non-working standby state, as shown in FIG. 5-*a*, the display area 502 does not have any functional display content; when the electric toothbrush is in a target working mode via the button 2 of the button area 503, with reference to FIG. 5-*b*, in the handle area 501, the light emitted by the corresponding light emitting element 6 penetrates through the light transmission plate 5 and the light transmission area 3 on the first coating 11 of the light transmission plate 5 in the target working mode, to project the shape of the light transmission area 3 to the second coating 12 of the shell 1 accurately and reliably to form a mark 4, and further, the mark 4 is made visible to a user due to the light transmission property of the second coating 12; the shape of the light transmission area 3 on the light transmission plate 5 can be flexibly adjusted by laser engraving; and visible mark 4 is realized in the display area 502 by adopting the imaging, projection and light transmission combined principle.

The handle area 501 is provided with a corresponding hole for installing the button 2; in order to improve the sealing performance at the hole, further referring to FIG. 6, a button ring 21 is arranged at the inner edge of the hole, so that the outer edge (in the circumferential direction) of the button 2 is in tight contact with the button ring 21; and a buffer washer (e.g., soft rubber 22) is arranged between the button 2 and the hole, so that when the button 2 is pressed, the outer edge of the inner side of its end face is tightly attached to the soft rubber 22, and its middle part is reliably jointed with the control panel 7.

Moreover, in order to further improve the joint reliability between the pressed button 2 and the control panel 7 when the button is pressed, a protrusion can be machined on the inner side of the end face of the button 2, and a recess corresponding to the protrusion can be formed on the soft rubber 22.

Described above are merely the specific embodiments of the present invention, but the protection scope of the present invention is not limited to this. Any variations or substitutions within the disclosed technical scope of the present invention that are readily conceivable to those skilled in the art shall fall within the protection scope of the present invention. Thus, the protection scope of the present invention shall be defined by the protection scope of the claims.

The invention claimed is:

1. An electric toothbrush handle, comprising:
   a shell, in an inner cavity of which at least one light emitting element is arranged; and
   a shading part, comprising:
   a light transmission plate arranged on a periphery of the at least one light emitting element;
   a first coating arranged on an outer surface and/or an inner surface of the light transmission plate; and
   a second coating arranged on an outer surface and/or an inner surface of the shell, wherein the second coating is adapted to transmit light of the light emitting element and shade ambient light;
   wherein a light transmission area in a set shape is formed at a position corresponding to each light emitting element in the first coating; and
   the light of the light emitting element is capable of penetrating through the light transmission area so that the shape of the light transmission area is visible via the shell.

2. The electric toothbrush handle of claim 1, wherein the shell is of a transparent structure.

3. The electric toothbrush handle of claim 1, wherein a driving control part is also arranged in the shell, and comprises:
   a motor, with a power output end connected with a brush head installed on the electric toothbrush handle, and used for driving the brush head into motion; and
   a control panel, used for controlling the motor and the light emitting element.

4. The electric toothbrush handle of claim 3, wherein the light transmission plate and the light emitting element are both fixed on the control panel.

5. The electric toothbrush handle of claim 3, wherein a support is also arranged in the shell;
   one side of the support is provided with a battery holder which is matched with a battery cover to form an installation space for a battery;
   the control panel is fixed on the other side of the support; and
   a tail end of the support is axially limited via a bottom cover.

6. The electric toothbrush handle of claim 3, wherein at least one switch for selecting a target working mode is also arranged on the shell, and the switch is electrically connected with the control panel.

7. An electric toothbrush, comprising an electric toothbrush handle and at least one brush head which can be installed at one end of the electric toothbrush handle, wherein the electric toothbrush handle comprising:
   a shell, in an inner cavity of which at least one light emitting element is arranged; and
   a shading part, comprising:
   a light transmission plate arranged on a periphery of the at least one light emitting element;
   a first coating arranged on an outer surface and/or an inner surface of the light transmission plate; and
   a second coating arranged on an outer surface and/or an inner surface of the shell, wherein the second coating is adapted to transmit light of the light emitting element and shade ambient light;
   wherein a light transmission area in a set shape is formed at a position corresponding to each light emitting element in the first coating; and
   the light of the light emitting element is capable of penetrating through the light transmission area so that the shape of the light transmission area is visible via the shell.

8. The electric toothbrush of claim 7, wherein the shell is of a transparent structure.

9. The electric toothbrush of claim 7, wherein a driving control part is also arranged in the shell, and comprises:
   a motor, with a power output end connected with the brush head installed on the electric toothbrush handle, and used for driving the brush head into motion; and
   a control panel, used for controlling the motor and the light emitting element.

10. The electric toothbrush of claim 9, wherein the light transmission plate and the light emitting element are both fixed on the control panel.

11. The electric toothbrush of claim 9, wherein a support is also arranged in the shell;
    one side of the support is provided with a battery holder which is matched with a battery cover to form an installation space for a battery;
    the control panel is fixed on the other side of the support; and
    a tail end of the support is axially limited via a bottom cover.

12. The electric toothbrush of claim 9, wherein at least one switch for selecting a target working mode is also arranged on the shell, and the switch is electrically connected with the control panel.

* * * * *